US005627154A

United States Patent [19]
Kelbaugh et al.

[11] Patent Number: 5,627,154

[45] Date of Patent: May 6, 1997

[54] **CALCIUM CHANNEL BLOCKING POLYPEPTIDES FROM *HETEROPODA VENATORIA***

[75] Inventors: Paul R. Kelbaugh, Niantic; Nicholas A. Saccomano, Ledyard; Robert A. Volkmann, Mystic, all of Conn.

[73] Assignee: Pfizer Inc., New York, N.Y.

[21] Appl. No.: 428,248

[22] PCT Filed: Aug. 16, 1993

[86] PCT No.: PCT/US93/07555

§ 371 Date: Apr. 27, 1995

§ 102(e) Date: Apr. 27, 1995

[87] PCT Pub. No.: WO94/10195

PCT Pub. Date: May 11, 1994

[51] Int. Cl.⁶ .................................................. A61K 38/00
[52] U.S. Cl. ............................................................ 514/12
[58] Field of Search .................................................. 514/12

[56] References Cited

PUBLICATIONS

Proceedings of The Indian Academy of Science; 97,pp. 231–237, (1988).
J. Biological Chemsitry, 265, pp. 861–867, (1990).

*Primary Examiner*—Edward J. Cain
*Attorney, Agent, or Firm*—P. C. Richardson; P. H. Ginsburg; B. C. Zielinski

[57] ABSTRACT

Polypeptides isolated from the venom of the *Heteropoda venanoria* spider block calcium channels in cells of various organisms and are useful in blocking said calcium channels in cells, per se, in the treatment of calcium channel-mediated diseases and conditions and in the control of invertebrate pests.

36 Claims, No Drawings and muscle cells of various organisms including invertebrates and vertebrates. This invention also relates to the use of said polypeptides and their salts in blocking calcium channels in cells such as cells in the nervous and muscular system of an organism, per se, and in the treatment of calcium channel mediated diseases and conditions in a mammal. Further, this invention relates to compositions comprising said polypeptides and salts thereof.

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
  ( A ) LENGTH: 30 amino acids
  ( B ) TYPE: amino acid
  ( C ) STRANDEDNESS: single
  ( D ) TOPOLOGY: linear ( i i ) MOLECULE TYPE: peptide ( v i ) ORIGINAL SOURCE:
  ( A ) ORGANISM: Heteropoda venatoria
  ( F ) TISSUE TYPE: venom ( x i ) SEQUENCE DESCRIPTION: SEQ ID NO: 1:

```
Asp Asp Cys Gly Gly Leu Phe Ser Gly Cys Asp Ser Asn Ala Asp Cys
1               5                   10                  15
Cys Glu Gly Tyr Val Cys Arg Leu Trp Cys Lys Tyr Lys Leu
                20                  25                  30
```

( 2 ) INFORMATION FOR SEQ ID NO: 2:

( i ) SEQUENCE CHARACTERISTICS:
  ( A ) LENGTH: 33 amino acids
  ( B ) TYPE: amino acid
  ( C ) STRANDEDNESS: single
  ( D ) TOPOLOGY: linear ( i i ) MOLECULE TYPE: peptide ( v i ) ORIGINAL SOURCE:
  ( A ) ORGANISM: Heteropoda venatoria
  ( F ) TISSUE TYPE: venom ( x i ) SEQUENCE DESCRIPTION: SEQ ID NO: 2:

```
Asp Cys Gly Thr Ile Trp His Tyr Cys Gly Thr Asp Gln Ser Glu Cys
1               5                   10                  15
Cys Glu Gly Trp Lys Cys Ser Arg Gln Leu Cys Lys Tyr Val Ile Asp
                20                  25                  30
Trp
```

( 2 ) INFORMATION FOR SEQ ID NO: 3:

( i ) SEQUENCE CHARACTERISTICS:
  ( A ) LENGTH: 37 amino acids
  ( B ) TYPE: amino acid
  ( C ) STRANDEDNESS: single
  ( D ) TOPOLOGY: linear ( i i ) MOLECULE TYPE: peptide ( v i ) ORIGINAL SOURCE:
  ( A ) ORGANISM: Heteropoda venatoria
  ( F ) TISSUE TYPE: venom ( x i ) SEQUENCE DESCRIPTION: SEQ ID NO: 3:

```
Asp Asp Asp Cys Gly Trp Ile Met Asp Asp Cys Thr Ser Asp Ser Asp
1               5                   10                  15
Cys Cys Pro Asn Trp Val Cys Ser Lys Thr Gly Phe Val Lys Asn Ile
                20                  25                  30
Cys Lys Tyr Glu Met
                35
```

( 2 ) INFORMATION FOR SEQ ID NO: 4:

( i ) SEQUENCE CHARACTERISTICS:
        ( A ) LENGTH: 36 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Heteropoda venatoria
        ( F ) TISSUE TYPE: venom ( x i ) SEQUENCE DESCRIPTION: SEQ ID NO: 4:

```
Ala  Asp  Cys  Gly  Trp  Leu  Phe  His  Ser  Cys  Glu  Ser  Asn  Ala  Asp  Cys
  1              5                        10                       15
Cys  Glu  Asn  Trp  Ala  Cys  Ala  Thr  Thr  Gly  Arg  Phe  Arg  Tyr  Leu  Cys
              20                       25                       30
Lys  Tyr  Gln  Ile
          35
```

( 2 ) INFORMATION FOR SEQ ID NO: 5:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Heteropoda venatoria
        ( F ) TISSUE TYPE: venom ( x i ) SEQUENCE DESCRIPTION: SEQ ID NO: 5:

```
Glu  Cys  Gly  Thr  Leu  Phe  Ser  Gly  Cys  Ser  Thr  His  Ala  Asp  Cys  Cys
  1              5                        10                       15
Glu  Gly  Phe  Ile  Cys  Lys  Leu  Trp  Cys  Arg  Tyr  Glu  Arg  Thr  Trp
              20                       25                       30
```

( 2 ) INFORMATION FOR SEQ ID NO: 6:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Heteropoda venatoria
        ( F ) TISSUE TYPE: venom ( x i ) SEQUENCE DESCRIPTION: SEQ ID NO: 6:

```
Asp  Asp  Cys  Gly  Thr  Leu  Phe  Ser  Gly  Cys  Asp  Thr  Ser  Lys  Asp  Cys
  1              5                        10                       15
Cys  Glu  Gly  Tyr  Val  Cys  His  Leu  Trp  Cys  Lys  Tyr  Lys
              20                       25
```

( 2 ) INFORMATION FOR SEQ ID NO: 7:

( i ) SEQUENCE CHARACTERISTICS:
        ( A ) LENGTH: 33 amino acids
        ( B ) TYPE: amino acid
        ( C ) STRANDEDNESS: single -continued ( D ) TOPOLOGY: linear ( i i ) MOLECULE TYPE: peptide ( v i ) ORIGINAL SOURCE:
        ( A ) ORGANISM: Heteropoda venatoria
        ( F ) TISSUE TYPE: venom ( x i ) SEQUENCE DESCRIPTION: SEQ ID NO: 7:

```
Asp Cys Gly Thr Ile Trp His Tyr Cys Gly Thr Asp Gln Ser Glu Cys
1               5                   10                      15
Cys Glu Gly Trp Lys Cys Ser Arg Gln Leu Cys Lys Tyr Val Ile Asp
                20              25                  30
Trp
```

( 2 ) INFORMATION FOR SEQ ID NO: 8:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Heteropoda venatoria
        ( F ) TISSUE TYPE: venom ( x i ) SEQUENCE DESCRIPTION: SEQ ID NO: 8:

```
Asp Asp Cys Gly Lys Leu Phe Ser Gly Cys Asp Thr Asn Ala Asp Cys
1               5                   10                      15
Cys Glu Gly Tyr Val Cys Arg Leu Trp Cys Lys Leu Asp Trp
                20              25                  30
```

( 2 ) INFORMATION FOR SEQ ID NO: 9:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Heteropoda venatoria
        ( F ) TISSUE TYPE: venom ( x i ) SEQUENCE DESCRIPTION: SEQ ID NO: 9:

```
Glu Cys Gly Thr Leu Phe Ser Gly Cys Ser Thr His Ala Asp Cys Cys
1               5                   10                      15
Glu Gly Phe Ile Cys Lys Leu Trp Cys Arg Tyr Glu Arg Thr Trp
                20              25                  30
```

CALCIUM CHANNEL BLOCKING POLYPEPTIDES FROM *HETEROPODA VENATORIA*

BACKGROUND OF THE INVENTION

This invention relates to polypeptides found in the venom of the *Heteropoda venatoria* spider and to polypeptides having substantially the same amino acid sequence and substantially the same activity as said polypeptides. The polypeptides and the pharmaceutically acceptable salts thereof block calcium channels in cells including neuronal and muscle cells of various organisms including invertebrates and vertebrates. This invention also relates to the use of said polypeptides and their salts in blocking calcium channels in cells such as cells in the nervous and muscular system of an organism, per se, and in the treatment of calcium channel mediated diseases and conditions in a mammal. Further, this invention relates to compositions comprising said polypeptides and salts thereof.

Compounds which are calcium antagonists have a variety of utilities. Calcium antagonists can find clinical application in the treatment of such conditions as angina, hypertension, cardiomyopathies, supraventricular arrhythmias, aesophogeal achalasia, premature labor and Raynaud's disease among others. See W. G. Nayler, *Calcium Antagonists*, Academic Press, Harcourt Brace Jovanovich Publishers, New York, N.Y. 1988, the teachings of which are incorporated herein by reference. Further, such compounds are useful in the study of the physiology of cells such as neuronal and muscle cells.

SUMMARY OF THE INVENTION

This invention concerns polypeptides found in the venom of the *Heteropoda venatoria* spider. The polypeptides of this invention and the fractions in which they are present according to this invention are as follows.

Heteropoda peptide AU 2 has the amino acid sequence, SEQ ID NO: 1. Heteropoda peptide AU 3 has the amino acid sequence, SEQ ID NO: 2. Heteropoda peptide AU 5A has the amino acid sequence, SEQ ID NO: 3. Heteropoda peptide AU 5B has the amino acid sequence, SEQ ID NO: 4. Heteropoda peptide AU 5C has the amino acid sequence, SEQ ID NO: 5. Heteropoda peptide KJ 1 has the amino acid sequence, SEQ ID NO: 6. Heteropoda peptide KJ 5 has the amino acid sequence, SEQ ID NO: 7. Heteropoda peptide KJ 6 has the amino acid sequence, SEQ ID NO: 8. Heteropoda peptide KJ 7 has the amino acid sequence, SEQ ID NO: 9.

The polypeptides of this invention block calcium channels in cells. Accordingly, these polypeptides are useful in blocking calcium channels in cells, per se. These polypeptides are also useful in the control of invertebrate pests and in the treatment of diseases and conditions in a mammal mediated by calcium channel function in cells.

Also within the scope of this invention are polypeptides which have substantially the same amino acid sequence and substantially the same calcium channel blocking activity as the polypeptides described above.

This invention also concerns pharmaceutical compositions comprising said polypeptides and methods of administering said polypeptides.

DETAILED DESCRIPTION OF THE INVENTION

Venom is obtained from the *Heteropoda venatoria* spider through the process of milking by electrical stimulation according to standard methods well known to those skilled in the art. It is preferred that the method employed is one which safeguards against contamination of the whole venom by abdominal regurgitant or hemolymph. Such methods are well known to those skilled in the art. The whole venom so obtained is stored in a frozen state at about −78° C. until used for purification as described below. Purification of the constituents from the whole venom is accomplished by reverse phase high performance liquid chromatography (HPLC) on a variety of preparative and semi-preparative columns such as C-4 and C-18 Vydac® columns (Rainin Instrument Co. Inc., Mack Road, Woburn, Mass. 01801). Peak detection is carried out monochromatically at 220–230 nm. Further analysis of the fractions can be accomplished with, for example, polychrome UV data collected with a Waters 990 diode array detector (Millipore Corporation, Waters Chromatography Division, 34 Maple Street, Milford, Mass. 01757). The fractions from the columns are collected by known methods such as through the use of an ISCO/ "FOXY" fraction collector and an ISCO 2159 peak detector (ISCO, 4700 Superior, Lincoln, Nebr. 68504). The fractions are collected in appropriately sized vessels such as sterile polyethylene laboratoryware. Concentration of the fractions is then accomplished by lyophilization from the eluant followed by lyophilization from water. Purity of the resulting constituent fractions then can be determined by chromatographic analysis using an analytical column with a gradient system which is more isocratic than the system used in the final purification of the fractions.

The polypeptides of the invention can be sequenced according to known methods. A general strategy for determining the primary structure includes, for example, the following steps. 1) Reduction and S-pyridylation of disulfide-bridged cysteine residues to enhance substrate susceptability to enzymatic attack. 2) Controlled cleavage of the peptide through single or multi-step enzymatic digestion. 3) Isolation and purification of peptide fragments via reverse phase high performance liquid chromatography (HPLC). 4) Characterization of peptide fragments through N-terminal sequencing and ion-spray mass spectrometry.

S-pyridylethylation of cysteine residues of the polypeptides under study can be performed, for example, in solution followed by amino acid sequencing of the polypeptides. One such procedure for S-pyridylethylation can be accomplished as described below.

About 1 to 10 μg of polypeptide is dissolved or diluted in up to 50 μl of a buffer prepared by mixing 1 part 1M TrisHCl, pH 8.5, containing 4 mM EDTA and 3 pans 8M guanidine HCl. 2.5 μl of 10% aqueous 2-mercaptoethanol is added and the mixture is incubated at room temperature in the dark under argon for two hours. After incubation, 2 μl of 4-vinylpyridine (fresh reagent stored under argon at −20° C.) is added and the mixture is incubated for another two hours at room temperature in the dark under argon. The mixture is then desalted, preferably by chromatography on a short, reverse phase column. The recovered alkylated polypeptide is then sequenced according to known methods.

Alternatively, the polypeptides can be sequenced after in situ reduction and pyridylethylation as described in V. Kruft et al., *Anal. Biochem.*, 193, 306 (1991).

Given the benefit of the disclosure herein with respect to the peptides present in fractions AU 2, AU 3, AU 5A, AU 5B, AU 5C, KJ 1, KJ 5, KJ 6 and KJ 7 of venom from *Heteropoda venatoria*, it is now possible to obtain said peptides by methods other than through isolation/purification from whole venom. The polypeptides of this invention can be produced using recombinant DNA techniques through the cloning of a coding sequence for said polypeptides or portions thereof. For example, hybridization probes which take advantage of the now known amino acid sequence information of said polypeptides can be employed according to methods well known to those skilled in the art to clone a coding sequence for the entire polypeptide. A combination of recombinant DNA techniques and in vitro protein synthesis can also be employed to produce the polypeptides of this invention. Such in vitro protein synthesis methods include, but are not limited to, use of an ABI 430A solid phase peptide synthesizer (Applied Biosystems, Inc., 850 Lincoln Center Drive, Foster City, Calif. 94404) employing standard Merrifield chemistry or other solid phase chemistries well known to those skilled in the art.

It is well known in the art that certain amino acid substitutions can be made in polypeptides which do not affect, or do not substantially affect, the function of said polypeptides. The exact substitutions which are possible vary from polypeptide to polypeptide. Determination of permissible substitutions is accomplished according to procedures well known to those skilled in the art. Thus, all polypeptides having substantially the same amino acid sequence and substantially the same calcium channel blocking activity are within the scope of this invention.

The polypeptides of this invention block calcium channels present in a variety of cells such as cells in the nervous and muscular system of invertebrates and vertebrates.

The ability of the polypeptides of this invention to block calcium channels is demonstrated by the following procedure. Cerebellar granule cells are prepared from the cerebellum of 8 day old rats (Wilkin et al., *Brain Res*, 115, 181–199, 1976). Squares (1 cm$^2$) of Aclar (Proplastics Inc., 5033 Industrial Ave., Wall, N.J. 07719) are coated with poly-L-lysine and placed in 12-well dishes that contain 1 ml of Eagles Basal Medium. The cells are dissociated and aliquots containing 6.25×10$^6$ cells are added to each well containing the squares of Aclar. Cytosine-beta-D-arabino furanoside (final concentration 10 μM) is added 24 hours after plating. The cells are used for fura2 analysis at 6, 7 and 8 days of culture. The cells (attached to the Aclar squares) are transferred to 12 well dishes containing 1 ml of 2 μM fura2/AM (Molecular Probes Inc., Eugene, Oreg. 97402) in HEPES buffer (containing 0.01% bovine serum albumin, 0.01% dextrose, pH 7.4, magnesium-free). The cells are incubated for 40 minutes at 37° C.; the fura2/AM-containing buffer is removed and replaced with 1 ml of the same buffer without fura2/AM. To a quartz cuvette is added 2.0 ml of prewarmed (37° C.) buffer. The cells on the Aclar are placed in the cuvette and the cuvette is inserted in a thermostatted (37° C.) holder equipped with a magnetic stirrer and the fluorescence is measured with a fluorescence spectrophotometer (Biomedical Instrument Group, University of Pennsylvania). The fluorescence signal is allowed to stabilize for about two minutes. Then 5–20 μl of a stock solution of the compound under study in phosphate buffered saline (PBS, pH 7.4) at appropriate concentration is added to the cuvette. Calibration of the fluorescent signals and fura2/AM leakage correction are performed using the established procedures of Nemeth et al., *J. Biol. Chem.*, 262, 5188 (1987) at the completion of each test. The maximum fluorescence value (Fmax) is determined by addition of ionomycin (35 μM) and the minimum fluorescence value (Fmin) is determined by the subsequent addition of EGTA (12 mM) to chelate calcium. Employing the foregoing procedure, calcium channel blocking by a subject polypeptide is shown to occur by a decrease in fluorescence upon addition of the subject polypeptide. The polypeptides of the invention exhibit low IC$_{50}$ values, under 3000 nm, for blocking calcium channels using this assay. For comparison, two known commercial calcium channel antagonists, Nifedipine and Verapamil, have IC$_{50}$ values of 33 nm and 4800 nm, respectively.

The polypeptides of this invention are useful as calcium channel blockers in cells, per se. As such, these polypeptides are also useful in the control of invertebrate pests and in the treatment of diseases and conditions mediated by calcium channels function in cells in a mammal such as angina, hypertension, cardiomyopathies, supraventricular arrhythmias, aesophogeal achalasia, premature labor and Raynaud's disease. Further, these polypeptides are useful in the study of the physiology of cells including, but not limited to, cells of the nervous and muscular system.

Also within the scope of this invention are the pharmaceutically acceptable salts of the polypeptides of this invention. Such salts are formed by methods well known to those skilled in the art. For example, base salts of the polypeptides can be prepared according to conventional methods.

When a polypeptide of this invention is to be administered to a mammal, it can be administered alone or in combination with pharmaceutically acceptable carriers or diluents in a pharmaceutical composition according to standard pharmaceutical practice. The polypeptides can be administered orally or parenterally with the parenteral route of administration being preferred for polypeptides. Parenteral administration includes intravenous, intramuscular, intraperitoneal, subcutaneous and topical administration.

For oral use of a polypeptide of this invention, the compound can be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents are lactose and dried corn starch. When aqueous suspensions are required for oral use, the active ingredient is combined with emulsifying and suspending agents. If desired, certain sweetening and/or flavoring agents can be added.

For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled to render the preparation isotonic.

When a polypeptide or salt thereof of this invention is used in a human subject, the daily dosage will normally be determined by the prescribing physician. Moreover, the dosage will vary according to the age, weight and response of the individual patient, as well as the severity of the patient's symptoms and the potency of the particular compound being administered.

When a polypeptide or salt thereof of this invention is used in control of invertebrate pests, said polypeptide is administered to said invertebrate directly or provided to the environment of said invertebrate. For example, a compound of this invention can be sprayed as a solution onto said invertebrate. The amount of compound necessary for control of said invertebrate will vary according to the invertebrate and environmental conditions and will be determined by the person applying the compound.

When a polypeptide or salt thereof of this invention is used in the physiological study of cells, said polypeptide is administered to the cells according to methods well known to those skilled in the art. For example, said polypeptide can be administered to cells in an appropriate physiological buffer. An appropriate concentration of a polypeptide of this invention for use in such studies is 200 µM. However, the concentration of said polypeptide in such studies may be greater than or much less than 200 µM. The amount of the polypeptide administered will be determined by the person skilled in the art according to well known methods.

EXAMPLES

EXAMPLE 1

Heteropoda peptide AU 2

A. Crude *Heteropoda venatoria* venom (~50 µl) was applied to a reversed phase HPLC column (Vydac®, C-18, 300 Å, 22×250 mm) and was operated using a biphasic linear gradient program from 80% A and 20% B to 65% A and 35% B over 80 minutes (A=0.1% trifluoroacetic acid (TFA), B=acetonitrile) with detection at 220 nm and a flow rate of 15 ml/minute. The desired fraction was collected from 36 to 38 minutes. Pooled fractions from individual runs were concentrated by lyophilization.

B. The material from fractionation A, above, derived from 50 µl of crude venom, was applied to a reversed phase HPLC column, (Vydac®, C-18, 300 Å, 22×250 mm) and was operated using an isocratic program of 76% A and 24% B (A=0.1% TFA, B=acetonitrile) with detection at 220 nm and a flow rate of 15 ml/minute. The desired fraction was collected from 29 to 31 minutes. Pooled like fractions from individual runs were concentrated by lyophilization, C. The structure of peptide AU 2 was determined and verified by the following methods. PTC amino acid analysis was carried out on 1–10 nmols in triplicate using the Waters Pico-Tag system. N-terminal sequencing was carried out on a pulse-liquid sequenator (ABI) on both native and reduced/pyridylethylated peptide. Mass spectral analysis was obtained from a SCI-EX API III ion spray mass spectrometer.

D. A pyridylethylated derivative of AU 2 suitable for N-terminal sequencing was prepared in the following manner. Peptide AU 2 (100 µg) was dissolved in 10 µl of buffer (1:3 ratio of 1M tris, pH 8.4, 4 µM EDTA-dibasic and 8M guanidine hydrochloride and was treated with 2.4 µl of a 1.41M (10% v/v) solution of 2-mercaptoethanol in buffer and was kept for 3 hours in the dark at room temperature. The reaction was then treated with 3.7 µl of a 0.93M solution of 4-vinylpyridine in buffer and was kept at room temperature in the dark for 18 hours. The reaction was diluted with 184 µl of 10% $CH_3CN/H_2O$ and was applied to an HPLC column (Vydac®, (C-18, 300 Å, 4.6×250 mm) which was operated using a biphasic linear gradient program from 90% A and 10% B to 65% A and 35% B over 30 minutes, then from 65% A and 35% B to 40% A and 60% B over 15 minutes (A=0.1% TFA, B=acetonitrile) with detection at 220 nm and a flow rate of 1.0 ml/minute. The desired fraction was collected at 27 to 28 minutes and was concentrated by lyophilization.

E. The data taken together affirm the structure of peptide AU 2 as shown below.
SEQ ID NO: 1, 30 residues, 6 cysteines, 3 disulfide bonds.
Calculated mass=331 7.74 (amide).
Observed mass=331 6.97 (ion spray m.s.).
Estimated pI=3.96.

EXAMPLE 2

Heteropoda peptide AU 3

A. Crude *Heteropoda venatoria* venom (~50 µl) was applied to a reversed phase HPLC column (Vydac®, C-18, 300 Å, 22×250 mm) and was operated using a biphasic linear gradient program from 80% A and 20% B to 65% A and 35% B over 80 minutes (A=0.1% trifluoroacetic acid (TFA), B=acetonitrile) with detection at 220 nm and a flow rate of 15 ml/minute. The desired fraction was collected from 41.5 to 43 minutes. Pooled fractions from individual runs were concentrated by lyophilization.

B. The structure of peptide AU 3 was determined and verified by the following methods. PTC amino acid analysis was carried out on 1–10 nmols in triplicate using the Waters Pico-Tag system. N-terminal sequencing was carried out on a pulse-liquid sequenator (ABI) on both native and reduced/pyridylethylated peptide. Mass spectral analysis was obtained from a SCI-EX API III ion spray mass spectrometer.

C. A pyridylethylated derivative of AU 3 suitable for N-terminal sequencing was generated in situ according to the method of V. Krufi et al., *Anal. Biochem.*, 193, 306 (1991).

D. The data taken together affirm the structure of peptide AU 3 as shown below.
SEQ ID NO: 2, 33 residues, 6 cysteines, 3 disulfide bonds.
Calculated mass=3910.35 (amide).
Observed mass=3909.94 (ion spray m.s.).
Estimated pI=4.54.

EXAMPLE 3

Heteropoda peptide AU 5A

A. Crude *Heteropoda venatoria* venom (~50 µl) was applied to a reversed phase HPLC column (Vydac®, C-18, 300 Å, 22×250 mm) and was operated using a biphasic linear gradient program from 80% A and 20% B to 65% A and 35% B over 80 minutes (A=0.1% trifluoroacetic acid (TFA), B=acetonitrile) with detection at 220 nm and a flow rate of 15 ml/minute. The desired fraction was collected from 46 to 47.5 minutes. Pooled fractions from individual runs were concentrated by lyophilization.

B. The material from fractionation A, above, derived from 50 µl of crude venom was applied to a semi-preparative potysulfoethyl (PolyLC 9.4×200 mm, 5µ) aspartamide column and was operated using a tripbasic linear gradient program from 20% A, 80% B and 0% C to 20% A, 55% B and 25% C (A=$CH_3CN$, B=5 mM $H_3PO_4/H_2O$, C=B+1M NaCl) over 45 minutes, with detection at 220 nm and a flow rate of 3.5 ml/minute. The desired fraction was collected from 16 to 17 minutes. Pooled fractions were desalted without concentration.

C. The material from fractionation B, above, derived from 50 µl of crude venom, was applied to a reversed phase HPLC column (Vydac®, C-18, 300 Å, 22×250 mm) and was operated using a linear gradient program from 100% A and 0% B to 80% A and 20% B over 10 minutes, then from 80% A and 20% B to 65% A and 35% B over 40 minutes (A=0.1% TFA, B=acetonitrile) with detection at 220 nm and a flow rate of 15 ml/minute. The desired fraction was collected from 40.5 to 41.5 minutes. Pooled like fractions from individual runs were concentrated by lyophilization.

D. The structure of peptide AU 5A was determined and verified by the following methods. PTC amino acid analysis was carried out on 1–10 nmols in triplicate using the Waters Pico-Tag system. N-terminal sequencing was carried out on a pulse-liquid sequenator (ABI) on both native and reduced/ pyridylethylated peptide. Mass spectral analysis was obtained from a SCI-EX API III ion spray mass spectrometer.

E. The data taken together affirm the structure of peptide AU 5A as shown below.
SEQ ID NO: 3, 37 residues, 6 cysteines, 3 disulfide bonds.
Calculated mass=4220.91 (amide).
Observed mass=4221.02 (ion spray m.s.).
Estimated pI=3.54.

EXAMPLE 4

Heteropoda peptide AU 5B

A. Crude *Heteropoda venatoria* venom (~50 μl) was applied to a reversed phase HPLC column (Vydac®, C-18, 300 Å, 22×250 mm) and was operated using a biphasic linear gradient program from 80% A and 20% B to 65% A and 35% B over 80 minutes (A=0.1% trifluoroacetic acid (TFA), B=acetonitrile) with detection at 220 nm and a flow rate of 15 ml/minute. The desired fraction was collected from 46 to 47.5 minutes. Pooled fractions from individual runs were concentrated by lyophilization.

B. The material from fractionation A, above, derived from 50 μl of crude venom was applied to a semi-preparative polysulfoethyl (PolyLC 9.4×200 mm, 5μ) aspartamide column and was operated using a triphasic linear gradient program from 20% A, 80% B and 0% C to 20% A, 55% B and 25% C over 45 minutes (A=CH$_3$CN, B=5 mM H$_3$PO$_4$/ H$_2$O, C=B+1M NaCl) with detection at 220 nm and a flow rate of 3.5 ml/minute. The desired fraction was collected from 28 to 29.5 minutes. Pooled fractions were desalted without concentration.

C. The material from fractionation B, above, derived from 50 μl of crude venom, was applied to a reversed phase HPLC column (Vydac®, C-18, 300 Å, 22×250 mm) and was operated using a linear gradient program from 100% A and 0% B to 80% A and 20% B over 10 minutes, then from 80% A and 20% B to 65% A and 35% B over 40 minutes (A=0.1% TFA, B=acetonitrile) with detection at 220 nm and a flow rate of 15 ml/minute. The desired fraction was collected from 42 to 43.5 minutes. Pooled like fractions from individual runs were concentrated by lyophilization.

D. The structure of peptide AU 5B was determined and verified by the following methods. PTC amino acid analysis was carried out on 1–10 nmols in triplicate using the Waters Pico-Tag system. N-terminal sequencing was carried out on a pulse-liquid sequenator (ABI) on both native and reduced/ pyridylethylated peptide. Mass spectral analysis was obtained from a SCI-EX API III ion spray mass spectrometer.

E. The data taken together affirm the structure of peptide AU 5B as shown below.
SEQ ID NO: 4, 36 residues, 6 cysteines, 3 disulfide bonds.
Calculated mass=4159.62 (amide).
Observed mass=4160.67 (ion spray m.s.).
Estimated pI=5.35.

EXAMPLE 5

Heteropoda peptide AU 5C

A. Crude *Heteropoda venatoria* venom (~50 μl) was applied to a reversed phase HPLC column (Vydac®, C-18, 300 Å, 22×250 mm) and was operated using a biphasic linear gradient program from 80% A and 20% B to 65% A and 35% B over 80 minutes (A=0.1% trifluoroacetic acid (TFA), B=acetonitrile) with detection at 220 nm and a flow rate of 15 ml/minute. The desired fraction was collected from 46 to 47.5 minutes. Pooled fractions from individual runs were concentrated by lyophilization.

B. The material from fractionation A, above, derived from 50 μl of crude venom was applied to a semi-preparative polysulfoethyl (PolyLC 9.4×200 mm, 5μ) aspartamide column and was operated using a tripbasic linear gradient program from 20% A, 80% B and 0% C to 20% A, 55% B and 25% C over 45 minutes (A=CH$_3$CN, B=5 mM H$_3$PO$_4$/ H$_2$O, C=B+1M NaCl) with detection at 220 nm and a flow rate of 3.5 ml/minute. The desired fraction was collected from 32 to 33 minutes. Pooled fractions were desalted without concentration.

C. The material from fractionation B, above, derived from 50 pl of crude venom, was applied to a reversed phase HPLC column (Vydac®, C-18, 300 Å, 22×250 mm) and was operated using a linear gradient program from 100% A and 0% B to 80% A and 20% B over 10 minutes, then from 80% A and 20% B to 65% A and 35% B over 40 minutes (A=0.1% TFA, B=acetonitrile) with detection at 220 nm and a flow rate of 15 ml/minute. The desired fraction was collected from 45 to 46.5 minutes. Pooled like fractions from individual runs were concentrated by lyophilization.

D. The structure of peptide AU 5C was determined and verified by the following methods. PTC amino acid analysis was carried out on 1–10 nmols in triplicate using the Waters Pico-Tag system. N-terminal sequencing was carried out on a pulse-liquid sequenator (ABI) on both native and reduced/ pyridylethylated peptide. Mass spectral analysis was obtained from a SCI-EX API III ion spray mass spectrometer.

E. A pyridylethylated derivative of AU 5C suitable for N-terminal sequencing was generated in situ according to the method of V. Kruft et al., *Anal. Biochem.*, 193, 306 (1991).

F. The data taken together affirm the structure of peptide AU 5C as shown below.
SEQ ID NO: 5, 31 residues, 6 cysteines, 3 disulfide bonds.
Calculated mass=3599.05 (amide).
Observed mass=3599.38 (ion spray m.s.).
Estimated pI=5.41.

EXAMPLE 6

Heteropoda peptide KJ 1

A. Crude *Heteropoda venatoria* venom (~50 μl) was applied to a reversed phase HPLC column (Vydac®, C-18, 300 Å, 22×250 mm) and was operated using a biphasic linear gradient program from 80% A and 20% B to 65% A and 35% B over 60 minutes (A=0.1% trifluoroacetic acid (TFA), B=acetonitrile) with detection at 220 nm and a flow rate of 15 ml/minute. The desired fraction was collected from 22 to 24 minutes. Pooled fractions from individual runs were concentrated by lyophilization.

B. The structure of peptide KJ 1 was determined and verified by the following methods. PTC amino acid analysis was carried out on 1–10 nmols in triplicate using the Waters Pico-Tag system. N-terminal sequencing was carried out on a pulse-liquid sequenator (ABI) on both native and reduced/ pyridylethylated peptide. Mass spectral analysis was obtained from a SCI-EX API III ion spray mass spectrometer.

C. The data taken together affirm the structure of peptide KJ 1 as shown below.
SEQ ID NO: 6, 29 residues, 6 cysteines, 3 disulfide bonds.
Calculated mass=3273.60 (amide).
Observed mass=3273.18 (ion spray m.s.).
Estimated pI=4.40.

EXAMPLE 7

Heteropoda peptide KJ 5

A. Crude *Heteropoda venatoria* venom (~50 μl) was applied to a reversed phase HPLC column (Vydac®, C-18, 300 Å, 22×250 mm) and was operated using a biphasic linear gradient program from 80% A and 20% B to 65% A and 35% B over 60 minutes (A=0.1% trifluoroacetic acid (TFA), B=acetonitrile) with detection at 220 nm and a flow rate of 15 ml/minute. The desired fraction was collected from 39 to 40.5 minutes. Pooled fractions from individual runs were concentrated by lyophilization.

B. The material from fractionation A, above, derived from 50 μl of crude venom, was applied to a reversed phase HPLC column (Vydac®, C-18, 300 Å, 22×250 mm) and was operated using a linear gradient program from 80% A and 20% B to 65% A and 35% B over 60 minutes (A=0.1% TFA, B=acetonitrile) with detection at 220 nm and a flow rate of 15 ml/minute. The desired fraction was collected from 39 to 40 minutes. Pooled like fractions from individual runs were concentrated by lyophilization.

C. The structure of peptide KJ 5 was determined and verified by the following methods. PTC amino acid analysis was carried out on 1–10 nmols in triplicate using the Waters Pico-Tag system. N-terminal sequencing was carried out on a pulse-liquid sequenator (ABI) on both native and reduced/pyridylethylated peptide. Mass spectral analysis was obtained from a SCI-EX API III ion spray mass spectrometer.

D. A pyridylethylated derivative of KJ 5 suitable for N-terminal sequencing was generated in situ according to the method of V. Kruft et al., *Anal. Biochem.*, 193, 306 (1991).

E. The data taken together affirm the structure of peptide KJ 5 as shown below.
SEQ ID NO: 7, 33 residues, 6 cysteines, 3 disulfide bonds.
Calculated mass=3910.35 (amide).
Observed mass=3909.94 (ion spray m.s.).
Estimated pI=4.54.

EXAMPLE 8

Heteropoda peptide KJ 6

A. Crude *Heteropoda venatoria* venom (~50 μl) was applied to a reversed phase HPLC column (Vydac®, C-18, 300 Å, 22×250 mm) and was operated using a biphasic linear gradient program from 80% A and 20% B to 65% A and 35% B over 60 minutes (A=0.1% trifluoroacetic acid (TFA), B=acetonitrile) with detection at 220 nm and a flow rate of 15 ml/minute. The desired fraction was collected from 43 to 44 minutes. Pooled fractions from individual runs were concentrated by lyophilization.

B. The structure of peptide KJ 6 was determined and verified by the following methods. PTC amino acid analysis was carried out on 1–10 nmols in triplicate using the Waters Pico-Tag system. N-terminal sequencing was carried out on a pulse-liquid sequenator (ABI) on both native and reduced/pyridylethylated peptide. Mass spectral analysis was obtained from a SCI-EX API III ion spray mass spectrometer.

C. A pyridylethylated derivative of KJ 6 suitable for N-terminal sequencing was generated in situ according to the method of V. Kruft et al., *Anal. Biochem.*, 193, 306 (1991).

D. The data taken together affirm the structure of peptide KJ 6 as shown below.
SEQ ID NO: 8, 30 residues, 6 cysteines, 3 disulfide bonds.
Calculated mass=3412.86 (amide).
Observed mass=3412.70 (ion spray m.s.).
Estimated pI=3.76.

EXAMPLE 9

Heteropoda peptide KJ 7

A. Crude *Heteropoda venatoria* venom (~50 μl) was applied to a reversed phase HPLC column (Vydac®, C-18, 300 Å, 22×250 mm) and was operated using a biphasic linear gradient program from 80% A and 20% B to 65% A and 35% B over 60 minutes (A=0.1% trifluoroacetic acid (TFA), B=acetonitrile) with detection at 220 nm and a flow rate of 15 ml/minute. The desired fraction was collected from 46 to 48.5 minutes. Pooled fractions from individual runs were concentrated by lyophilization.

B. The material from fractionation A, above, derived from 50 μl of crude venom, was applied to a reversed phase HPLC column (Vydac®, C-18, 300 Å, 22×250 mm) and was operated using an isocratic program of 75% A and 25% B (A=0.1% TFA, B=acetonitrile) with detection at 220 nm and a flow rate of 3.5 ml/minute. The desired fraction was collected from 55 to 68 minutes. Pooled like fractions from individual runs were concentrated by lyophilization.

C. The structure of peptide KJ 7 was determined and verified by the following methods. PTC amino acid analysis was carried out on 1–10 nmols in triplicate using the Waters Pico-Tag system. N-terminal sequencing was carried out on a pulse-liquid sequenator (ABI) on both native and reduced/pyridylethylated peptide. Mass spectral analysis was obtained from a SCI-EX API III ion spray mass spectrometer.

D. A pyridylethylated derivative of KJ 7 suitable for N-terminal sequencing was generated in situ according to the method of V. Kruft et al., *Anal. Biochem.*, 193, 306 (1991).

E. The data taken together affirm the structure of peptide KJ 7 as shown below.
SEQ ID NO: 9, 31 residues, 6 cysteines, 3 disulfide bonds.
Calculated mass=3599.05 (amide).
Observed mass=3599.38 (ion spray m.s.).
Estimated pI=5.41.

We claim:

1. A substantially pure polypeptide comprising the amino acid sequence, SEQ ID NO: 1, or a polypeptide having substantially the same amino acid sequence and substantially the same calcium channel blocking activity as said polypeptide, or a pharmaceutically acceptable salt thereof.

2. A substantially pure polypeptide according to claim 1 having the amino acid sequence, SEQ ID NO: 1, or a pharmaceutically acceptable salt thereof.

3. A method of blocking calcium channels in a cell comprising administering to said cell a calcium channel blocking amount of a polypeptide according to claim 1.

4. A method according to claim 3 wherein said cell is in the nervous system of a mammal.

5. A substantially pure polypeptide comprising the amino acid sequence, SEQ ID NO: 2, or a polypeptide having substantially the same amino acid sequence and substantially the same calcium channel blocking activity as said polypeptide, or a pharmaceutically acceptable salt thereof.

6. A substantially pure polypeptide according to claim 5 having the amino acid sequence, SEQ ID NO: 2, or a pharmaceutically acceptable salt thereof.

7. A method of blocking calcium channels in a cell comprising administering to said cell a calcium channel blocking amount of a polypeptide according to claim 5.

8. A method according to claim 7 wherein said cell is in the nervous system of a mammal.

9. A substantially pure polypeptide comprising the amino acid sequence, SEQ ID NO: 3, or a polypeptide having substantially the same amino acid sequence and substantially the same calcium channel blocking activity as said polypeptide, or a pharmaceutically acceptable salt thereof.

10. A substantially pure polypeptide according to claim 9 having the amino acid sequence, SEQ ID NO: 3, or a pharmaceutically acceptable salt thereof.

11. A method of blocking calcium channels in a cell comprising administering to said cell a calcium channel blocking amount of a polypeptide according to claim 9.

12. A method according to claim 11 wherein said cell is in the nervous system of a mammal.

13. A substantially pure polypeptide comprising the amino acid sequence, SEQ ID NO: 4, or a polypeptide having substantially the same amino acid sequence and substantially the same calcium channel blocking activity as said polypeptide, or a pharmaceutically acceptable salt thereof.

14. A substantially pure polypeptide according to claim 13 having the amino acid sequence, SEQ ID NO: 4, or a pharmaceutically acceptable salt thereof.

15. A method of blocking calcium channels in a cell comprising administering to said cell a calcium channel blocking amount of a polypeptide according to claim 13.

16. A method according to claim 15 wherein said cell is in the nervous system of a mammal.

17. A substantially pure polypeptide comprising the amino acid sequence, SEQ ID NO: 5, or a polypeptide having substantially the same amino acid sequence and substantially the same calcium channel blocking activity as said polypeptide, or a pharmaceutically acceptable salt thereof.

18. A substantially pure polypeptide according to claim 17 having the amino acid sequence, SEQ ID NO: 5, or a pharmaceutically acceptable salt thereof.

19. A method of blocking calcium channels in a cell comprising administering to said cell a calcium channel blocking amount of a polypeptide according to claim 17.

20. A method according to claim 19 wherein said cell is in the nervous system of a mammal.

21. A substantially pure polypeptide comprising the amino acid sequence, SEQ ID NO: 6, or a polypeptide having substantially the same amino acid sequence and substantially the same calcium channel blocking activity as said polypeptide, or a pharmaceutically acceptable salt thereof.

22. A substantially pure polypeptide according to claim 21 having the amino acid sequence, SEQ ID NO: 6, or a pharmaceutically acceptable salt thereof.

23. A method of blocking calcium channels in a cell comprising administering to said cell a calcium channel blocking amount of a polypeptide according to claim 21.

24. A method according to claim 23 wherein said cell is in the nervous system of a mammal.

25. A substantially pure polypeptide comprising the amino acid sequence, SEQ ID NO: 7, or a polypeptide having substantially the same amino acid sequence and substantially the same calcium channel blocking activity as said polypeptide, or a pharmaceutically acceptable salt thereof.

26. A substantially pure polypeptide according to claim 25 having the amino acid sequence, SEQ ID NO: 7, or a pharmaceutically acceptable salt thereof.

27. A method of blocking calcium channels in a cell comprising administering to said cell a calcium channel blocking amount of a polypeptide according to claim 25.

28. A method according to claim 27 wherein said cell is in the nervous system of a mammal.

29. A substantially pure polypeptide comprising the amino acid sequence, SEQ ID NO: 8, or a polypeptide having substantially the same amino acid sequence and substantially the same calcium channel blocking activity as said polypeptide, or a pharmaceutically acceptable salt thereof.

30. A substantially pure polypeptide according to claim 29 having the amino acid sequence, SEQ ID NO: 8, or a pharmaceutically acceptable salt thereof.

31. A method of blocking calcium channels in a cell comprising administering to said cell a calcium channel blocking amount of a polypeptide according to claim 29.

32. A method according to claim 31 wherein said cell is in the nervous system of a mammal.

33. A substantially pure polypeptide comprising the amino acid sequence, SEQ ID NO: 9, or a polypeptide having substantially the same amino acid sequence and substantially the same calcium channel blocking activity as said polypeptide, or a pharmaceutically acceptable salt thereof.

34. A substantially pure polypeptide according to claim 33 having the amino acid sequence, SEQ ID NO: 9, or a pharmaceutically acceptable salt thereof.

35. A method of blocking calcium channels in a cell comprising administering to said cell a calcium channel blocking amount of a polypeptide according to claim 33.

36. A method according to claim 35 wherein said cell is in the nervous system of a mammal.

* * * * *